(12) United States Patent
Tiverios et al.

(10) Patent No.: US 11,098,258 B2
(45) Date of Patent: *Aug. 24, 2021

(54) PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCKS

(71) Applicant: Fulcrum BioEnergy, Inc., Pleasanton, CA (US)

(72) Inventors: Peter G. Tiverios, Anderson, SC (US); Stephen H. Lucas, Foristell, MO (US); Lewis L. Rich, Seneca, SC (US)

(73) Assignee: Fulcrum BioEnergy, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,536

(22) Filed: Jul. 6, 2020

(65) Prior Publication Data

US 2020/0332206 A1  Oct. 22, 2020

Related U.S. Application Data

(60) Continuation of application No. 16/458,928, filed on Jul. 1, 2019, now Pat. No. 10,704,002, which is a (Continued)

(51) Int. Cl.
*C10L 1/04* (2006.01)
*B01J 19/00* (2006.01)
(Continued)

(52) U.S. Cl.
CPC . *C10L 1/04* (2013.01); *B01J 8/00* (2013.01); *B01J 19/0006* (2013.01);
(Continued)

(58) Field of Classification Search
CPC ..... C10J 3/721; C10J 3/26; C10J 3/466; C10J 2300/1628; C10J 2300/1634;
(Continued)

(56) References Cited

U.S. PATENT DOCUMENTS 5,494,653 A  2/1996 Paisley
5,666,891 A  9/1997 Titus et al.
(Continued)

FOREIGN PATENT DOCUMENTS

EP   0221679 A2   5/1987
EP   1526165 A1   4/2005
(Continued)

OTHER PUBLICATIONS

Baral et al., "Assessing the Climate Mitigation Potential of Biofuels Derived from Residues and Wastes in the European Context", Jan. 2014.
(Continued)

*Primary Examiner* — Jafar F Parsa
(74) *Attorney, Agent, or Firm* — DLA Piper LLP (US)

(57) ABSTRACT

Processes for producing high biogenic concentration Fischer-Tropsch liquids derived from the organic fraction of municipal solid wastes (MSW) feedstock that contains a relatively high concentration of biogenic carbon (derived from plants) and a relatively low concentration of non-biogenic carbon (derived from fossil sources) wherein the biogenic content of the Fischer-Tropsch liquids is the same as the biogenic content of the feedstock.

9 Claims, 9 Drawing Sheets

Related U.S. Application Data continuation of application No. 15/682,368, filed on Aug. 21, 2017, now Pat. No. 10,344,232, which is a continuation of application No. 15/077,782, filed on Mar. 22, 2016, now Pat. No. 9,738,579, which is a division of application No. 14/842,729, filed on Sep. 1, 2015, now Pat. No. 10,760,018, which is a continuation of application No. 14/799,522, filed on Jul. 14, 2015, now abandoned, which is a continuation-in-part of application No. 14/138,635, filed on Dec. 23, 2013, now Pat. No. 9,458,073, which is a continuation of application No. 13/023,505, filed on Feb. 8, 2011, now Pat. No. 8,614,257.

(60) Provisional application No. 61/302,516, filed on Feb. 8, 2010.

(51) Int. Cl.

| | |
|---|---|
| *C10J 3/26* | (2006.01) |
| *C10J 3/72* | (2006.01) |
| *C10K 1/10* | (2006.01) |
| *C10K 1/16* | (2006.01) |
| *B01J 8/00* | (2006.01) |
| *C07C 29/151* | (2006.01) |
| *C10G 2/00* | (2006.01) |
| *C10G 47/00* | (2006.01) |
| *C10J 3/46* | (2006.01) |
| *C10J 3/48* | (2006.01) |
| *C10J 3/82* | (2006.01) |
| *C10K 1/00* | (2006.01) |
| *C10K 3/04* | (2006.01) |
| *C10K 3/00* | (2006.01) |
| *C10L 1/08* | (2006.01) |

(52) U.S. Cl.
CPC ............ *C07C 29/1518* (2013.01); *C10G 2/32* (2013.01); *C10G 2/34* (2013.01); *C10G 47/00* (2013.01); *C10J 3/26* (2013.01); *C10J 3/466* (2013.01); *C10J 3/485* (2013.01); *C10J 3/721* (2013.01); *C10J 3/82* (2013.01); *C10K 1/004* (2013.01); *C10K 1/005* (2013.01); *C10K 1/101* (2013.01); *C10K 1/16* (2013.01); *C10K 3/001* (2013.01); *C10K 3/04* (2013.01); *C10L 1/08* (2013.01); *B01J 2208/00115* (2013.01); *C10J 2300/0903* (2013.01); *C10J 2300/0906* (2013.01); *C10J 2300/0946* (2013.01); *C10J 2300/0959* (2013.01); *C10J 2300/0976* (2013.01); *C10J 2300/1628* (2013.01); *C10J 2300/1634* (2013.01); *C10J 2300/1643* (2013.01); *C10J 2300/1659* (2013.01); *C10J 2300/1665* (2013.01); *C10J 2300/1671* (2013.01); *C10J 2300/1675* (2013.01); *C10J 2300/1815* (2013.01); *C10J 2300/1853* (2013.01); *C10L 2200/0469* (2013.01); *C10L 2200/0492* (2013.01); *C10L 2270/023* (2013.01); *C10L 2270/026* (2013.01); *C10L 2270/04* (2013.01); *C10L 2290/04* (2013.01); *C10L 2290/10* (2013.01); *C10L 2290/42* (2013.01); *C10L 2290/54* (2013.01); *C10L 2290/543* (2013.01); *Y02E 20/16* (2013.01); *Y02E 50/10* (2013.01); *Y02E 50/30* (2013.01); *Y02P 20/129* (2015.11); *Y02P 20/133* (2015.11); *Y02P 30/00* (2015.11)

(58) Field of Classification Search
CPC ....... C10J 2300/1665; C10J 2300/1671; C10L 1/04; C10L 2290/04; C10L 2290/10; C10L 2290/54; C10L 2270/04; C10L 2270/026; C10L 2270/023; C10L 2200/0492; C10G 47/00; C10G 2/32; C10G 2/34; Y02E 50/18; Y02E 50/30; Y02E 50/32; Y02E 50/343; C07C 29/1518; C07C 31/04; C07C 31/08; C10K 3/04; C10K 1/005; C10K 1/004

See application file for complete search history.

(56) References Cited

U.S. PATENT DOCUMENTS

| | | |
|---|---|---|
| 5,707,508 A | 1/1998 | Surma et al. |
| 5,756,957 A | 5/1998 | Titus et al. |
| 5,785,923 A | 7/1998 | Surma et al. |
| 5,798,497 A | 8/1998 | Titus et al. |
| 5,811,752 A | 9/1998 | Titus et al. |
| 5,847,353 A | 12/1998 | Titus et al. |
| 5,908,564 A | 6/1999 | Titus et al. |
| 6,018,471 A | 1/2000 | Titus et al. |
| 6,037,560 A | 3/2000 | Titus et al. |
| 6,215,678 B1 | 4/2001 | Titus et al. |
| 6,475,375 B1 | 11/2002 | Dancuart |
| 6,630,113 B1 | 10/2003 | Surma |
| 7,846,979 B2 | 12/2010 | Rojey et al. |
| 7,888,540 B2 | 2/2011 | Deluga et al. |
| 8,604,088 B2 | 12/2013 | Lucas et al. |
| 8,604,089 B2 | 12/2013 | Lucas et al. |
| 8,614,257 B2 | 12/2013 | Lucas et al. |
| 8,624,069 B2 | 1/2014 | Diebold et al. |
| 9,458,073 B2 | 10/2016 | Lucas et al. |
| 9,738,579 B2 | 8/2017 | Lucas et al. |
| 10,344,232 B2 | 7/2019 | Lucas et al. |
| 10,344,233 B2 | 7/2019 | Lucas et al. |
| 10,704,002 B2 | 7/2020 | Lucas et al. |
| 10,760,018 B2 | 9/2020 | Tiverios et al. |
| 2003/0083390 A1 | 5/2003 | Shah et al. |
| 2004/0182003 A1 | 9/2004 | Bayle et al. |
| 2005/0109672 A1 | 5/2005 | Bauldreay et al. |
| 2005/0250862 A1 | 11/2005 | Bayle et al. |
| 2005/0261382 A1 | 11/2005 | Keyser et al. |
| 2006/0112616 A1 | 6/2006 | Noll et al. |
| 2007/0117195 A1 | 5/2007 | Warner et al. |
| 2008/0115415 A1 | 5/2008 | Agrawal et al. |
| 2008/0168706 A1 | 7/2008 | Rusek et al. |
| 2008/0178784 A1 | 7/2008 | Farone |
| 2008/0244962 A1 | 10/2008 | Abhari et al. |
| 2008/0275278 A1 | 11/2008 | Clark |
| 2009/0000185 A1 | 1/2009 | Aulich et al. |
| 2009/0056225 A1 | 3/2009 | Schinski |
| 2009/0188165 A1 | 7/2009 | Ariyapadi et al. |
| 2009/0259082 A1 | 10/2009 | Deluga et al. |
| 2010/0018113 A1 | 1/2010 | Bohlig et al. |
| 2010/0018116 A1 | 1/2010 | Mahjoob |
| 2010/0022669 A1 | 1/2010 | Cohn et al. |
| 2010/0031560 A1 | 2/2010 | Calabrese et al. |
| 2010/0036181 A1 | 2/2010 | Diebold et al. |
| 2010/0040510 A1 | 2/2010 | Randhava et al. |
| 2010/0179315 A1 | 7/2010 | Medoff |
| 2011/0113676 A1 | 5/2011 | Mackay et al. |
| 2011/0288352 A1 | 11/2011 | Peters et al. |
| 2012/0020846 A1 | 1/2012 | Blevins et al. |
| 2012/0172458 A1 | 7/2012 | Onishi |
| 2012/0208902 A1 | 8/2012 | Kresnyak et al. |
| 2012/0291351 A1 | 11/2012 | Bool et al. |
| 2013/0090393 A1 | 4/2013 | Bracht et al. |
| 2013/0109765 A1 | 5/2013 | Jiang et al. |
| 2014/0088204 A1 | 3/2014 | Tanaka |
| 2014/0213669 A1 | 7/2014 | Herrmann |
| 2014/0224706 A1 | 8/2014 | Do et al. |
| 2015/0376510 A1 | 12/2015 | Lucas et al. |
| 2017/0058222 A1 | 3/2017 | Lucas et al. |
| 2019/0345400 A1 | 11/2019 | Lucas et al. |

(56) References Cited

U.S. PATENT DOCUMENTS

2020/0255754 A1 8/2020 Tiverios et al.
2020/0392420 A1 12/2020 Tiverios et al.

FOREIGN PATENT DOCUMENTS

| JP | 62-169887 A | 7/1987 |
|---|---|---|
| JP | 2006-334584 A | 12/2006 |
| JP | 2007-211097 A | 8/2007 |
| JP | 2008-260832 A | 10/2008 |
| JP | 2011-526323 A | 10/2011 |
| WO | WO 2007/005954 A1 | 1/2007 |
| WO | WO 2009/009388 A2 | 1/2009 |
| WO | WO 2009/009389 A2 | 1/2009 |
| WO | WO 2009/013232 A2 | 1/2009 |
| WO | WO 2009/114752 A1 | 9/2009 |
| WO | WO 2009/158539 A1 | 12/2009 |
| WO | 2011/024650 A1 | 3/2011 |
| WO | WO 2011/097648 A2 | 8/2011 |
| WO | WO 2011/128513 A1 | 10/2011 |
| WO | WO 2014/001580 A1 | 1/2014 |
| WO | WO 2017/011025 A1 | 1/2017 |
| WO | WO 2017/039741 A1 | 3/2017 |

OTHER PUBLICATIONS

Clark, Jim, "Le Chatelier's Principle", retrieved from http://www.chemguide.co.uk/physical/equilibria/lechatelier.html, 2002 (modified Apr. 2013).
Drift et al., "Entrained Flow Gasification of Biomass—Ash behaviour, feeding issues, and system analyses", ECN Publication, ECN Report No. ECN-C—04-039, Apr. 2004, pp. 1-58.
Dutta, Abhijit et al., "Techno-economics of the Production of Mixed Alcohols from Lignocellulosic Biomass via High-Temperature Gasification", Environmental Progress & Sustainable Energy, vol. 29, No. 2, pp. 163-174, published online May 11, 2010.
Nuss et al., "Environmental Implications and Costs of Municipal Solid Waste-Derived Ethylene", Journal of Industrial Ecology, vol. 17, No. 6, pp. 912-925, first published Nov. 2013.
Phillips, S. et al., "Thermochemical Ethanol via Indirect Gasification and Mixed Alcohol Synthesis of Lignocellulosic Biomass," National Renewable Energy Laboratory, Technical Report NREL/TP-510-41168, Apr. 2007, 132 pages.
International Search Report and Written Opinion in International Application No. PCT/US2011/024108, dated Oct. 20, 2011.
International Search Report and Written Opinion in International Application No. PCT/US2015/058471, dated Jan. 21, 2016.
International Search Report and Written Opinion in International Application No. PCT/US2015/067950, dated Mar. 17, 2016.
Extended European Search Report in European Application No. 11740545.6, dated Nov. 20, 2013.
Examination Report in European Application No. 11740545.6, dated Jul. 22, 2016.
Examination Report in European Application No. 11740545.6, dated Jul. 27, 2017.
Preliminary Office Action in Brazilian Application No. 1120180008362, dated Sep. 30, 2019.
Extended European Search Report in European Application No. 15898468.2, dated Feb. 20, 2019.
Examination Report in European Application No. 15898468.2 dated Apr. 8, 2020.
Notice of Reasons for Rejection in Japanese Application No. 2018-521818, dated Jul. 12, 2019.
Notice of Reasons for Rejection in Japanese Application No. 2018-521818, dated Jun. 22, 2020.
Examination Report in Australian Application No. 2015408249, dated Dec. 11, 2019.
Extended European Search Report in European Application No. 15903290.3, dated Feb. 20, 2019.
Examination Report in European Application No. 15903290.3 dated Apr. 9, 2020.
Notice of Reasons for Rejection in Japanese Application No. 2018-530482, dated Jul. 12, 2019.
Notice of Reasons for Rejection in Japanese Application No. 2018-530482, dated Jun. 22, 2020.
Office Action in U.S. Appl. No. 13/023,497, dated May 24, 2013.
Notice of Allowance in U.S. Appl. No. 13/023,497, dated Aug. 9, 2013.
Office Action in U.S. Appl. No. 13/023,505, dated May 23, 2013.
Notice of Allowance in U.S. Appl. No. 13/023,505, dated Aug. 2, 2013.
Office Action in U.S. Appl. No. 13/023,510, dated May 23, 2013.
Notice of Allowance in U.S. Appl. No. 13/023,510, dated Aug. 2, 2013.
Notice of Allowance in U.S. Appl. No. 14/138,635, dated Feb. 1, 2016.
Notice of Allowance in U.S. Appl. No. 14/138,635, dated Jun. 9, 2016.
Office Action in U.S. Appl. No. 14/947,820, dated May 13, 2016.
Office Action in U.S. Appl. No. 14/947,820, dated Dec. 8, 2016.
Office Action in U.S. Appl. No. 14/947,820, dated Jul. 6, 2017.
Office Action in U.S. Appl. No. 14/947,820, dated Feb. 9, 2018.
Office Action in U.S. Appl. No. 14/947,820, dated Sep. 17, 2018.
Office Action in U.S. Appl. No. 14/947,820, dated Mar. 29, 2019.
Office Action in U.S. Appl. No. 14/947,820, dated Oct. 11, 2019.
Office Action in U.S. Appl. No. 14/947,820, dated May 5, 2020.
Office Action in U.S. Appl. No. 14/842,729, dated Feb. 23, 2016.
Office Action in U.S. Appl. No. 14/842,729, dated Sep. 6, 2016.
Office Action in U.S. Appl. No. 14/842,729, dated Jan. 8, 2018.
Office Action in U.S. Appl. No. 14/842,729, dated Aug. 28, 2018.
Office Action in U.S. Appl. No. 14/842,729, dated Mar. 28, 2019.
Office Action in U.S. Appl. No. 14/842,729, dated Jan. 3, 2020.
Notice of Allowance in U.S. Appl. No. 14/842,729, dated Jun. 29, 2020.
Office Action in U.S. Appl. No. 15/077,782, dated May 16, 2016.
Notice of Allowance in U.S. Appl. No. 15/077,782, dated Mar. 14, 2017.
Office Action in U.S. Appl. No. 15/682,368, dated Jan. 2, 2018.
Office Action in U.S. Appl. No. 15/682,368, dated Oct. 4, 2018.
Notice of Allowance in U.S. Appl. No. 15/682,368, dated Feb. 19, 2019.
Office Action in U.S. Appl. No. 15/791,045, dated Dec. 28, 2017.
Office Action in U.S. Appl. No. 15/791,045, dated Oct. 4, 2018.
Notice of Allowance in U.S. Appl. No. 15/791,045, dated Feb. 20, 2019.
Office Action in U.S. Appl. No. 16/458,928, dated Aug. 21, 2019.
Notice of Allowance in U.S. Appl. No. 16/458,928 dated Feb. 28, 2020.
Office Action in U.S. Appl. No. 16/505,428, dated Feb. 20, 2020.
Office Action in U.S. Appl. No. 16/505,428, dated Sep. 17, 2020.
Notice of Allowance in U.S. Appl. No. 16/505,428, dated Dec. 11, 2020.
Isotope Energy Education, https://energyeducation.ca/encyclopedia/Isotope, 2018.
Office Action in U.S. Appl. No. 14/947,820, dated Dec. 28, 2020.
Decision of Rejection in Japanese Application No. 2018-521818, dated Jan. 18, 2021.
Decision of Rejection in Japanese Application No. 2018-530482, dated Jan. 18, 2021.
Notice of Reasons for Rejection in Japanese Application No. 2020-003690, dated Jan. 25, 2021.
Examination Report in European Application No. 15898468.2 dated Mar. 16, 2021.

PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCKS

CROSS-REFERENCE TO RELATED APPLICATION

This application is a continuation of U.S. patent application Ser. No. 16/458,928 filed Jul. 1, 2019, entitled PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCKS, which is a continuation of U.S. patent application Ser. No. 15/682,368 filed Aug. 21, 2017, entitled PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCKS now U.S. Pat. No. 10,344,232, which is a continuation of U.S. patent application Ser. No. 15/077,782 filed Mar. 22, 2016, entitled PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCKS now U.S. Pat. No. 9,738,579, which is a divisional of U.S. patent application Ser. No. 14/842,729 filed Sep. 1, 2015, entitled PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCK, which is a continuation of U.S. patent application Ser. No. 14/799,522 filed Jul. 14, 2015, entitled PROCESSES FOR PRODUCING HIGH BIOGENIC CONCENTRATION FISCHER-TROPSCH LIQUIDS DERIVED FROM MUNICIPAL SOLID WASTES (MSW) FEEDSTOCK now Abandoned, which is a continuation-in-part of U.S. patent application Ser. No. 14/138,635 filed Dec. 23, 2013, entitled GAS RECYCLE LOOPS IN PROCESS FOR CONVERTING MUNICIPAL SOLID WASTE INTO ETHANOL now U.S. Pat. No. 9,458,073, which is a continuation of U.S. patent application Ser. No. 13/023,505 filed Feb. 8, 2011, entitled PRODUCT RECYCLE LOOPS IN PROCESS FOR CONVERTING MUNICIPAL SOLID WASTE INTO ETHANOL now U.S. Pat. No. 8,614,257, which claims benefit of U.S. Provisional Patent Application No. 61/302,516 filed Feb. 8, 2010, entitled PROCESSES FOR CONVERTING MUNICIPAL SOLID WASTE INTO ETHANOL, the disclosure of these applications are incorporated by reference hereinto.

The application is further related to the following U.S. patent applications. U.S. patent application Ser. No. 13/023,497, filed Feb. 8, 2011, entitled "Processes For Recovering Waste Heat From Gasification Systems For Converting Municipal Solid Waste Into Ethanol," which issued on Dec. 10, 2013 as U.S. Pat. No. 8,604,088 B2, and U.S. patent application Ser. No. 13/023,510, filed Feb. 8, 2011, entitled "Gas Recycle Loops in Process For Converting Municipal Solid Waste Into Ethanol," which issued on Dec. 10, 2013 as U.S. Pat. No. 8,604,089 B2. These applications are incorporated by reference hereinto.

TECHNICAL FIELD

The subject matter relates generally to processes, systems, and facilities for converting municipal solid wastes (MSW) into fuel.

BACKGROUND

Municipal solid waste (MSW) includes all solid materials disposed by municipalities. While some of this waste is recycled, the majority is typically dumped in landfills, where it decomposes over a period of decades or even centuries. It has been recognized that municipal solid waste contains organic materials that have energy content. If MSW is left untreated in landfills, the energy content can be drained slowly from the landfill by bacterial processes, which not only dissipate the concentrated energy but, also, produce methane, a strong greenhouse gas. Some landfills have sought to collect methane, which may be used for fuel; however, the conversion to methane takes place on long time scales, wastes much of the internal energy of the MSW, and is rather ineffective in recovering much of the available energy content of the MSW.

The earliest and most common method of recovering energy from MSW is incineration. Incineration includes the combustion of MSW or refuse-derived fuel (RDF) to produce heat, which typically powers a turbine to produce electricity. Byproducts of incineration include fly ash, bottom ash, and flue gases containing dangerous pollutants including sulfur compounds, CO2, which is a green-house gas, acid gases as well as metals, metal compounds and particulates. Fly ash and bottom ash are typically discarded in landfills. Some harmful flue gases and particulates can be scrubbed from the incineration flue stream prior to discharge into the atmosphere.

Another method of recovering energy from MSW is pyrolysis, which involves heating the organic portions of the MSW, so that thermally unstable compounds are chemically decomposed into other compounds. Those compounds mix with other volatile components to form a pyrolysis gas that typically includes tars, alkenes, aromatic hydrocarbons, sulfur compounds, steam, and carbon dioxide. The solid residue from pyrolysis process includes coke (residual carbon), which can then be burned or used as a gasification feedstock.

A related method for recovering energy from MSW is gasification. Gasification involves converting at least a fraction of the MSW into a synthesis gas ("syngas') composed mainly of carbon monoxide carbon dioxide, and hydrogen. Gasification technology has existed for some centuries. In the nineteenth century, for instance, coal and peat were often gasified into "town gas" that provided a flammable mix of carbon monoxide (CO), methane ($CH_4$) and hydrogen ($H_2$) that was used for cooking, heating and lighting. During World Wars I and II, biomass and coal gasifies were used to produce CO and $H_2$ to meet transportation needs. Sometimes, some of the syngas was converted directly in to liquid transportation fuels using the Fisher-Tropsch process. With the discovery of vast quantities of domestic oil and natural gas following World War II, coal and biomass gasification were no longer cost-competitive and all but disappeared.

Gasification has been applied directly to the MSW but, in other cases, the MSW is first pyrolyzed, and then subjected to a secondary gasification process. Gasification of MSW generally includes a mechanical processing step that removes recyclables and other materials that have low or no energy content. Then, the processed feedstock is heated in a gasifier in the presence of a gasification agent (including at least some oxygen and possibly steam). Gasifiers may have a number of configurations. For example, fixed-bed gasifiers place the feedstock in a fixed bed, and then contact it with a stream of a gasification agent in either a counter-current ("up draft") or co-current ("down draft") manner. Gasifiers may also use fluidized bed reactors.

Another method of gasifying MSW is treatment in the presence of oxygen with a high-temperature plasma. Such systems may convert the MSW to syngas, leaving vitrified wastes and metals as byproduct.

To create hydrocarbons as synthetic fuels, a known method for converting syngas into synthetic fuels is the catalytic Fischer-Tropsch (F-T) process. This process produces a mixture of hydrocarbons which could be further refined to produce liquid transportation fuels.

With numerous detrimental effects of greenhouse gases being increasingly documented, there is a clear need to reduce energy production from fossil fuels, particularly from petroleum and coal-derived fuel sources. To encourage the reduction of fossil fuel usage, governments are promoting the usage of fuels derived from renewable organic sources rather than fossil-based sources.

The Environmental Protection Agency (EPA) in the United States has mandated a Renewable Fuel Standard ("RFS") under which cellulosic-based fuels generate Cellulosic RINs (renewable identification numbers) which are a form of compliance credits for Obligated Parties (e.g., refineries). Under the RFS, the Obligated Parties are required to blend an increasing amount of cellulosic fuel into fossil-derived fuels.

To determine the biogenic percentage content of fuels, the EPA requires tests that use radiocarbon dating methods. More particularly, current the USEPA regulations, at Section 8.1426(f)(9), require parties to use Method B or Method C of ASTM D 6866 to perform radiocarbon dating to determine the renewable fraction of the fuel.

BRIEF SUMMARY OF THE INVENTION

The present disclosure generally relates to processes and methods for converting organic materials, such as are contained in MSW, into fuels. More particularly, the present disclosure relates to processes for producing high biogenic concentration Fischer-Tropsch liquids and the respective upgraded fuel products derived from the organic fraction of municipal solid wastes (MSW) feedstocks that contain relatively high concentrations of biogenic carbon (derived from plants) and a relatively low concentration of non-biogenic carbon (derived from fossil sources) along with other non-carbonaceous materials. In practice, the relatively high concentration of biogenic carbon is up to about 80% biogenic carbon. Particularly noteworthy is that the high biogenic concentration Fischer-Tropsch liquids contain the same relatively high concentration of biogenic carbon as the feedstock derived from MSW.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted, based on this disclosure, in view of the common knowledge within this field.

Various embodiments, including additions and modifications to the illustrated embodiment, of the present inventions are described herein in the context of converting feedstock derived from MSW waste into fuels.

In the Drawings:

FIG. 1 shows one embodiment of an overall system for producing high biogenic concentration Fischer-Tropsch liquids derived from municipal solid wastes (MSW) feedstock; that contains a relatively high concentration of biogenic carbon and a relatively low concentration of non-biogenic carbons along with other non-carbonaceous materials;

FIG. 2 shows an example of one embodiment of a gasification island;

FIG. 3 shows an example of one embodiment of a syngas conditioning system;

FIG. 4A shows an example of one embodiment of a CO2/H2S removal system;

FIG. 4B shows an example of another embodiment of a CO2/H2S removal system;

FIG. 5 shows an example of one embodiment of a system for generating F-T liquids;

FIG. 6 shows an example of one embodiment of a system for producing refined F-T liquids from the system of FIG. 5.

DETAILED DESCRIPTION

Figure 1:
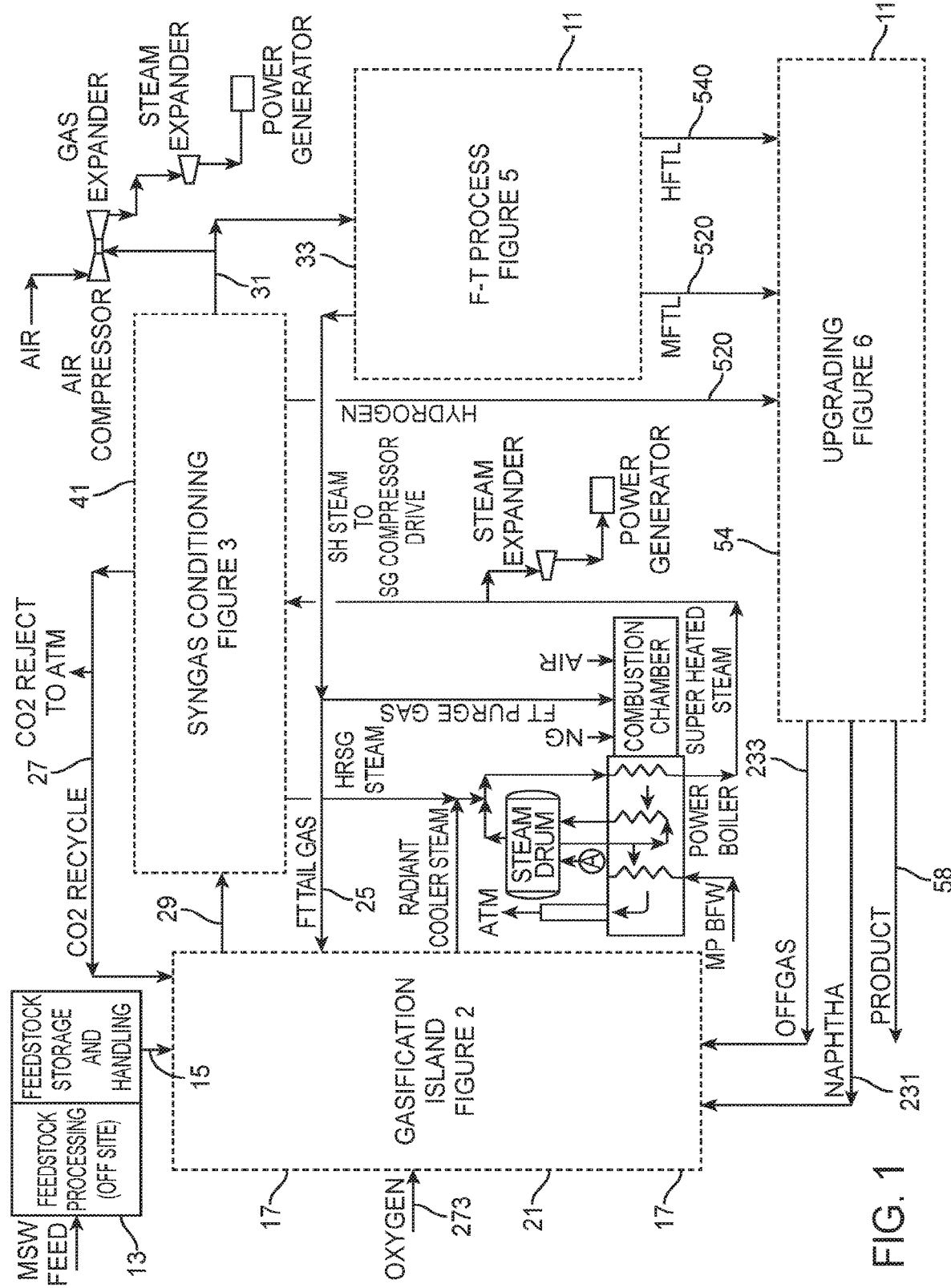

Those of ordinary skill in the art will understand that the following detailed description is illustrative only and is not intended to be in any way limiting. Other embodiments of the present inventions will readily suggest themselves to such skilled persons having the benefit of this disclosure, in light of what is known in the relevant arts, the provision and operation of information systems for such use, and other related areas. Reference will now be made in detail to exemplary implementations of the present inventions as illustrated in the accompanying drawings.

In the interest of clarity, not all of the routine features of the exemplary implementations described herein are shown and described. It will of course, be appreciated that in the development of any such actual implementation, numerous implementation-specific decisions must be made in order to achieve the specific goals of the developer, such as compliance with regulatory, safety, social, environmental, health, and business-related constraints, and that these specific goals will vary from one implementation to another and from one developer to another. Moreover, it will be appreciated that such a developmental effort might be complex and time-consuming, but would nevertheless be a routine undertaking of engineering for those of ordinary skill in the art having the benefit of this disclosure.

Throughout the present disclosure, relevant terms are to be understood consistently with their typical meanings established in the relevant art. However, without limiting the scope of the present disclosure, further clarifications and descriptions are provided for relevant terms and concepts as set forth below:

The term municipal solid waste (MSW) as used herein has the same meaning as the term is understood by one of skill in the art. An example of MSW is the solid waste that is obtained from the collection of commercial and household trash. In its raw form, MSW need not be entirely solid, as it may contain entrained or absorbed liquids, or liquids in containers or other enclosed spaces. One of skill in the art will understand that MSW will have a broad range of compositions, and that the source of MSW need not necessarily be from a municipality. For purposes of this disclosure, other organic waste materials and various biomass materials such as vegetative matter, may be equivalent to MSW.

The term stream as used herein means any fluid or solid moving or en route, directly or indirectly, from one location to another. A stream is still a stream even if it is temporarily stationary.

Reference to a portion of a stream or material refers to any portion of the stream or material, including the stream or material in its entirety. A portion of a stream or material may be mixed with other compositions of matter and the mixture will be considered to comprise the portion of the original stream or material.

The term in fluid communication with as used herein includes without limitation both direct and indirect fluid communication, such as, for example, through an intermediate process unit.

The term unit as used herein means part of a system, and may for example comprise a unit operation, a system or group of unit operations, a plant, etc.

The term syngas (synthesis gas) as used herein has the same meaning as the term is used by one of skill in the art. For example, syngas may comprise a combination of carbon monoxide, hydrogen, carbon dioxide and possibly other components such as, without limitation, water vapor, sulfur- or nitrogen-containing compounds, methane and other alkanes, hydrocarbons, acid gases, halogens and particulates.

The term separator as used herein refers to any process unit known in the art for performing a separation process and, depending upon context, can include distillation columns, membrane separation systems, ion exchange adsorption systems, thermal adsorption, pressure swing adsorption, molecular sieves, flash drums, absorption or adsorption columns, wet scrubbers, venturi scrubbers, centrifuges, chromatographs, or crystallizers. Separators may separate vapors from liquids, liquids from liquids, vapors from liquids from solids, solids from solids, or fluids from solids.

The term heat exchanger as used herein includes without limitation any heat exchanger or heat exchange device known in the art, and more broadly, any device which raises the enthalpy or internal energy of a first composition of matter, decreases the enthalpy or internal energy of a second composition of matter, and transfers heat from the second composition of matter to the first composition of matter. Various heat exchange means are disclosed herein, all of which are encompassed within this term. The term also includes combinations or series of multiple heat exchange means. It includes, without limitation, shell and tube heat exchangers, air or "fin-fan" coolers, refrigeration units, chillers, cooling towers, steam generators, boilers, plate heat exchangers, adiabatic wheel heat exchangers, plate fin heat exchangers, fluid heat exchangers, waste heat recovery units of any kind, or phase change heat exchangers of any kind. They may operate in a countercurrent, parallel, crosscurrent configuration, or any other flow configuration, and may involve separation of two fluids or direct contact between two fluids, or the use of an intermediate fluid (such as water, hot oil, molten salt, etc.) to transfer heat from one fluid to another.

The term compressor as used herein includes anything that is understood as a compressor in the normal sense of that term. In general, however, the term includes any device that raises a fluid from a first pressure to a second, higher pressure, either adiabatically or non-adiabatically. It may include any kind of compressor or pump, including without limitation, centrifugal or axial, or positive displacement (such as reciprocating, diaphragm, or rotary gear). The term may also include one or more stages of a multi-stage compressor. The term compressor used in the singular may also refer to multiple compressors arranged in series and/or parallel.

In FIG. 1, the Numeral 11 Designates an Overall System for Producing High Biogenic concentration Fischer-Tropsch liquids derived from municipal solid wastes (MSW) feedstock that contains a relatively high concentration of biogenic carbon and a relatively low concentration of non-biogenic carbons along with other non-carbonaceous materials.

At the head of the system 11, a MSW feedstock producing facility, generally designated by the numeral 13, is provided for removing non-biogenic derived carbon materials and non-carbonaceous materials from MSW to produce a segregated feedstock that contains a relatively high concentration of biogenic carbon and a relatively low concentration of non-biogenic carbon along with other non-carbonaceous materials found in MSW.

In the preferred embodiment, the Feedstock Processing Facility 13 will process inbound MSW and separate materials into the following categories:

Feedstock Material, sorted from MSW stream to be used for conversion into fuel;

Recoverable Material, including but not limited to ferrous and nonferrous metals, cardboard, plastics, paper, and other recyclable materials that can be sorted and shipped to the commodities markets; and Residual Material, which is the remainder of the material not recycled or used as feedstock, which can be sent to landfill.

By recovering plastics such as High Density Polyethylene (HDPE) and Polyethylene Terephthalate (PET) among others, the percentage of non-biogenic carbon in the feedstock is reduced as the percentage of fossil based plastics is reduced. Thus, the feedstock processing facility functions to provide a highly biogenic feedstock material that can be gasified into syngas. For the reasons explained above, the biogenic percentage content of the feedstock has a significant impact on the economic value of the cellulosic fuel.

In the feedstock processing unit 13, the waste material may be sized, separated, and processed to remove materials that are not useful in the process, or which might reduce its efficiency. For example, the system removes metals, inorganic materials, and wet materials such as food waste or agricultural products. Such materials may, for example, be recycled or sent to a landfill. Some of the food waste and agricultural materials which are high in biogenic content could be dried and added back to the feed stream along with other materials.

As indicated in the drawing, the Feedstock Processing Facility 13 can be physically separate facility from the other portions of the system shown in FIG. 1. As an example, the Feedstock Processing Facility 13 can be as described in co-pending U.S. patent application Ser. No. 14/138,635 for Product Recycle Loops in Process for Converting Municipal Solid Waste into Ethanol, the disclosure of which is incorporated herein by reference.

Although the feedstock may vary greatly in composition, example nominal values for the composition of the material remaining after the feedstock is recycled and sorted are listed in Table 1 below.

TABLE 1

Example Ultimate Chemical Composition of Feedstock

| Feedstock Constituent | Approx. Weight (Percent) |
| --- | --- |
| C | 45.4 |
| H | 5.7 |
| O | 33.8 |
| N | 0.7 |
| S | 0.11 |
| Cl | 0.09 |
| Ash | 4.21 |
| Metal | 1.4 |
| $H_2O$ | 8.6 |

The residual materials preferably excluded by the processing, storage, and handling process may include, for instance, metals, rocks, dirt, glass, concrete, and PVC. Preferably, under normal conditions, the reject rate will run between about 10% and about 55% of the total feed rate to the material processing unit. Preferably, they will be individually separated from the feedstock, deposited in a container, and transported to a landfill or composting operation, or sent for recycling or disposal off-site in accordance with applicable governmental regulations.

An important point is that a bio-refinery, generally designated by the numeral 17, is fed with a stream 15 containing relatively high concentration of biogenic carbon and the relatively low concentration of non-biogenic carbons along with other non-carbonaceous materials from the municipal solid wastes. In practice, the relatively high concentration of biogenic carbon is up to about 80% biogenic carbon.

The remainder of the system depicted in FIG. 1 is the bio-refinery 17 for converting the stream 15 of processed feedstock into a stream 19 of Fischer-Tropsch liquids. Particularly noteworthy is that the high biogenic concentration Fischer-Tropsch liquids contain the same relatively high concentration of biogenic carbon as the input stream 15. In other words, percentage-wise, no non-biogenic carbon is added to the Fischer-Tropsch liquids in the production system and, indeed, some may be eliminated.

In the illustrated embodiment, the bio-refinery 17 includes a gasification system, generally designated by the numeral 21 and sometimes referred to herein as the Gasification Island (GI), for converting feedstock derived from MSW into syngas and further processing that syngas through a hydrocarbon reformer (HR), as will described below, to generate a high biogenic content syngas. It should be noted that the gasification system 21 receives streams 231 and 235 that carry recycled hydrocarbon products and intermediate products, respectively, to the HR. Also, the GI 21 receives a stream 27 that carries recycled CO2 to its stage 1 and stage 2, both of which will be described in detail below. Also as will be explained further below, the recycled CO2 is used for moderating the water-gas-shift reaction within the steam reformer in the GI 21 and as a purge gas for instruments, instrument systems and MSW feeder systems. Further, the GI 21 receives stream 273 of oxygen and a stream 25 of F-T tail gas.

In the gasification island 21, generally speaking, the biogenic carbon is converted into biogenic syngas by a combination of steam reforming, sub-stoichiometric carbon oxidation and hydrocarbon reformation. The syngas product, including CO, H2 and CO2, is carried by stream 29 in the illustrated embodiment. The gasification reactions occurring in the GI 21 will be further described below.

The syngas stream 29 is processed in a syngas conditioning system 41, as will be described in more detail below, to provide a syngas feed stream 31 to an F-T reactor system 33. It should be noted that the syngas conditioning system 41 provides the CO2 recycle stream 27 for recycling CO2 back to the GI 21.

The output from the F-T reactor system 33 comprises F-T fluids, including a Medium Fischer Tropsch Liquid (MFTL) stream 520 and a Heavy Fischer Tropsch liquid (HFTL) stream 540, both of which are F-T hydrocarbons. Any unreacted syngas can be recycled in the F-T reactor 33 as will be described below. Further, the output of the F-T reactor system 33 includes the afore-mentioned stream 25 of F-T tail gas.

The bio-refinery includes a hydrogen recovery system to remove hydrogen that is needed for upgrading from the conditioned syngas. A portion of the conditioned syngas flows through a combination membrane/PSA unit to yield a high purity hydrogen stream for the upgrading unit. The recovered hydrogen (permeate) from the membrane is fed to a PSA unit and the retentate is combined with bypass syngas and fed forward to the FT reactor. The recovered hydrogen is fed to the PSA unit where a relatively pure hydrogen stream is produced (>99.5% H2) and the PSA reject stream is routed to the suction of the syngas compressor for recovery of the reject syngas.

The bio-refinery 17 in FIG. 1 further includes an upgrading system 54 for receiving the F-T fluids from the F-T system 33. In the illustrated embodiment, both the Heavy Fischer Tropsch liquid (HFTL) stream 540 and the Medium Fischer Tropsch Liquid (MFTL) stream 520 are fed to the upgrading system 54. The F-T liquids output liquid from the upgrading system 54 is carried by the stream 58 in the illustrated embodiment. In practice, the F-T liquids can include naphtha, diesel, Synthetic Paraffinic Kerosene (SPK), heavier alkanes along with iso-alkanes, oxygenates, and olefins or combinations of all of these components. Other outputs from the upgrading system 54 are the afore-mentioned stream 231 of naphtha and the stream 233 of off gas.

Figure 2:
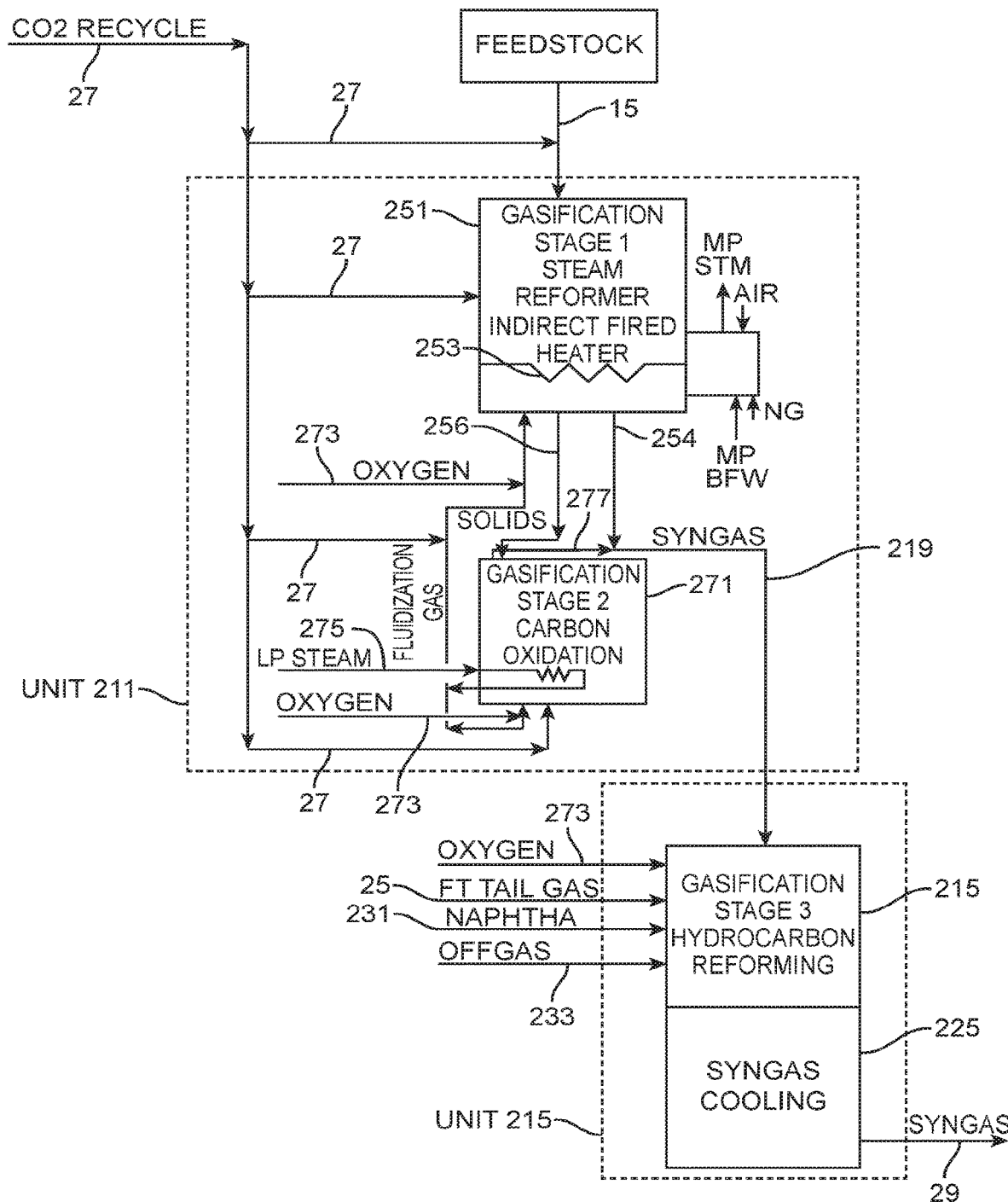

The gasification island system 21, as shown in detail in FIG. 2, implements a 3-stage gasification process. In the preferred embodiment, the 3-stage gasification process includes:

a. Stage 1—steam reforming;
b. Stage 2—sub-stoichiometric carbon oxidation to gasify unreacted carbon after steam reforming; and
c. Stage 3—hydrocarbon reforming.

In the illustrated embodiment, the gasification unit, generally designated by the numeral 211, includes stage 1 and 2 units, generally designated by the numerals 251 and 271, respectively. It can be understood that unit 251 is a steam reformer wherein gasification is accomplished. Further it can be understood that unit 271 is a carbon oxidation system wherein unreacted carbon from the stage 1 gasification is converted into syngas sub-stoichiometrically. Also in the gasification island 21, hydrocarbon reforming is provided in a third stage by a hydrocarbon reforming system generally designated by the numeral 215.

Steam reformer 251 selectively receives the stream 15 of processed feedstock and produces a stream 219 of syngas. Also, the gasification unit 211 receives streams 27 of recycled CO2. In the gasification unit 211, the recovered high biogenic CO2 in stream 27 can be used to assist in fluidizing the bed materials, moderating the water-gas-shift reaction and purging instruments in the steam reformer 251, in the sub-stoichiometric carbon oxidation unit 271 and in the hydrocarbon reformer 215. Also, the recovered high biogenic CO2 in stream 27 can be added to stream 15 of processed feedstock as shown.

As mentioned above, the gasification unit 211 in the embodiment of FIG. 2 includes the steam reformer 251 and the sub-stoichiometric carbon oxidation unit 271. It is the steam reformer 251 that initially receives the steam 15 of processed feedstock. Also, it is the steam reformer 251 that initially receives the steam 273 of oxygen. Preferably, the steam reformer 251 includes an indirect heat source 253. The output streams from the steam reformer 251 include a stream 254 of syngas and a stream 256 of solids. The syngas stream 254 is carried to the hydrocarbon reforming unit 215 with the stream 219. The solids stream 256, primarily comprised of ash and fine char, is carried to the sub-stoichiometric carbon oxidation unit 271.

In the preferred embodiment, the steam reformer 251 is a fluidized bed system that utilizes superheated steam, CO2, and O2 as the bed-fluidizing medium. In another embodiment only steam and O2 are used as a bed-fluidizing medium. Preferably, externally-fired indirect heaters 253 maintain the reformer bed temperature and provide much of the energy to support the endothermic reactions required in the gasification process. The process gas stream can exit the steam reformer 251 through a series of cyclones. Preferably, an internal cyclone separates and returns the majority of any entrained bed media to the reformer fluidized bed while a second external cyclone collects unreacted char for further conversion to syngas in the sub-stoichiometric carbon oxidation unit 271. Preferably, flue gas from the steam reformer's indirect heaters is used in a fire tube boiler to generate steam for plant use.

The illustrated hydrocarbon reformer unit 215 receives the syngas stream 219 and produces the afore-mentioned primary stream 29 of syngas containing CO, H2 and CO2 along with trace constituents. Further, the hydrocarbon reformer unit 215 receives stream 273 of oxygen and stream 25 of F-T tail gas. Finally, the hydrocarbon reformer unit 215 receives the aforementioned streams 231 of naphtha and 233 of off gas.

The hydrocarbon reformer unit 215 operates to recover the biogenic carbon by thermally dissociating hydrocarbons at temperatures greater than 2200 degrees F. Heat for the hydrocarbon reformer is provided by oxidation of carbon monoxide and hydrogen. It may be noted that these reactions are exothermic.

The hydrocarbon reformer unit 215, in the embodiment of FIG. 2, includes a syngas cooling section 225. The syngas cooling section can comprise, for example, a radiant slagging cooler or a recycle syngas slagging quencher.

In preferred practice, the hydrocarbon reforming unit 215 is a refractory-lined vessel with oxygen gas burner/mixer which operates in the range of 1800° F. to 3000° F. to assure all hydrocarbon compounds in the gas stream, including tars are converted to syngas, sulfur compounds are converted to $H_2S$, and the water gas shift reactions approach equilibrium. In the hydrocarbon reforming unit 215, the F-T tail gas purged from the F-T reaction loop, the purification system off gas, and stream 231 of vaporized naphtha are converted back to CO and $H_2$.

The sub-stoichiometric carbon oxidation unit 271, in addition to receiving the solids stream 256, receives the stream 27 of recycled CO2 stream and a stream 273 of oxygen. Heating in the carbon sub-stoichiometric oxidation unit 271 is provided by sub-stoichiometric oxidation of the unreacted carbon. A stream 275 of low pressure steam is superheated in the sub-stoichiometric carbon oxidation unit and used as fluidization steam for both stage 1 and stage 2 gasification. The output of the sub-stoichiometric carbon oxidation unit 271 is syngas stream 277 which, in the illustrated embodiment, joins with the syngas stream 254 from steam reformer 251 to form syngas stream 219 which is fed to the hydrocarbon reformer unit 215.

In the preferred embodiment, the sub-stoichiometric carbon oxidation unit 271 utilizes a fluidized bed in which oxygen is added with the fluidization steam and CO2 to further convert fine char to syngas. The gasses generated in and passing through the sub-stoichiometric carbon oxidation unit 271 pass through an external cyclone and re-enter the main syngas stream 219. Preferably, the ash removed in the cyclone is cooled and transported to a collection silo for offsite disposal. Heat exchangers, submerged in the fluid bed of the sub-stoichiometric carbon oxidation unit 271 remove some heat by superheating low-pressure steam to 1100° F. for use in the fluidization bed steam reformer 251 and the fluidization bed of the unit 271 itself.

In operation of the system of FIG. 2, within the fluidized bed of the steam reformer 251, externally fired heaters rapidly heat the circulating bed media and the feedstock entering the vessel. Almost immediately, the feedstock undergoes drying and pyrolysis, thereby creating gaseous and solid (char) products. The gaseous pyrolysis products undergo water-gas shift reactions and together with simultaneous steam reforming of the solid char material, produce a syngas primarily made up of H2, CO, CO2, and some hydrocarbons. Most remaining char reacts with superheated steam and oxygen to produce syngas. Char that escapes the steam reformer is separated via a cyclone and dropped into the sub-stoichiometric carbon oxidation unit for additional gasification and conversion. The steam reformer and the sub-stoichiometric carbon oxidation unit utilize internal and external cyclones to separate and retain bed media that becomes entrained in the process gas stream. From the steam reformer 251 and the sub-stoichiometric carbon oxidation unit 271, the syngas flows via stream 219 to the hydrocarbon reformer unit 215 to convert any remaining char, hydrocarbons, and tars into syngas.

As mentioned above, the output of the hydrocarbon reformer unit 215 is the syngas stream 29 which is fed to the syngas conditioning system 41 which will now be described in conjunction with FIG. 3.

Figure 3:
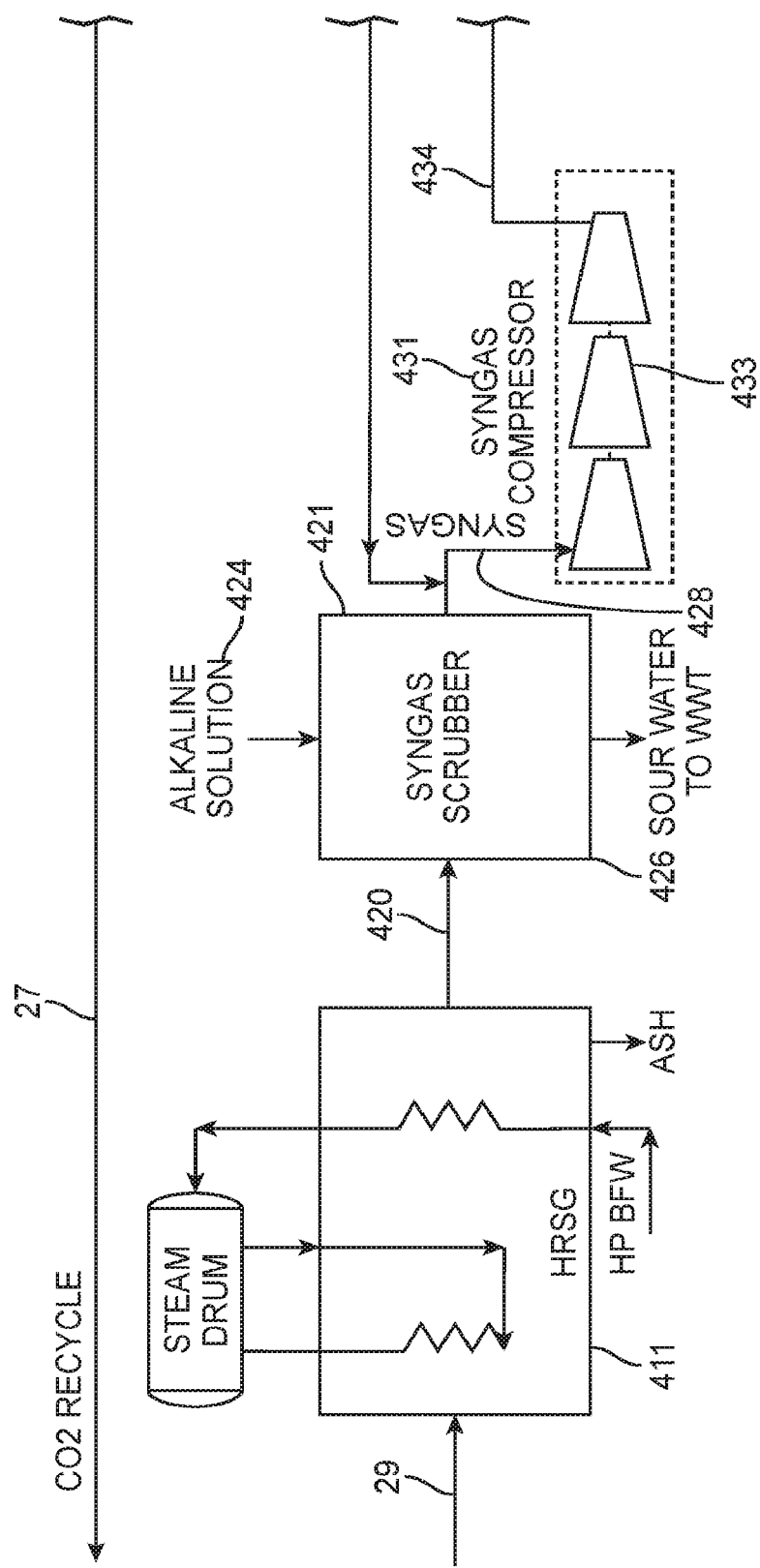
Figure 3:
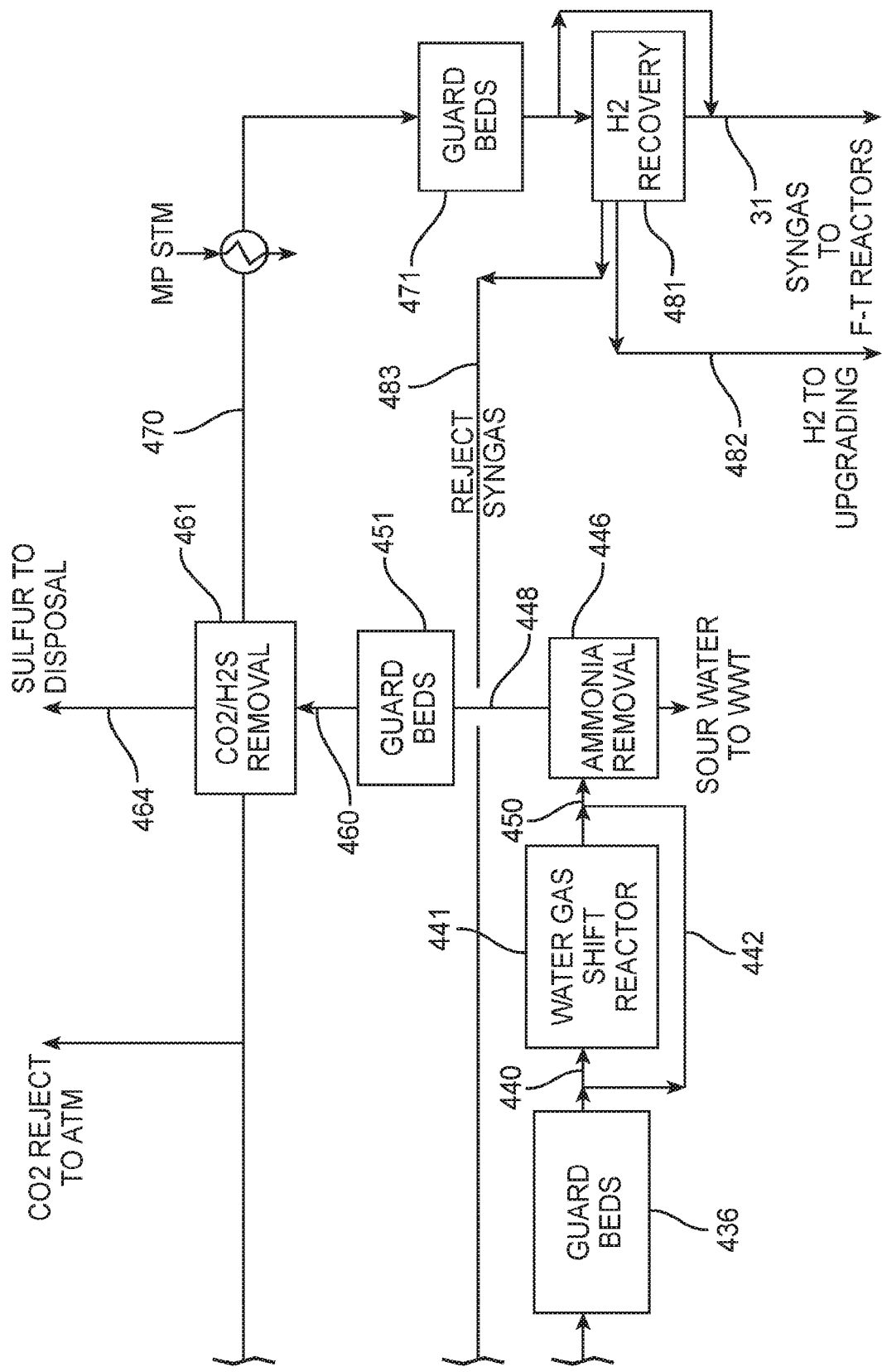

As shown in FIG. 3, the exemplary syngas conditioning system, which has been generally designated by the numeral 41, receives the primary syngas stream 29 and conditions that stream to produce the gaseous feed stream 31 to F-T reactors. In the illustrated embodiment, the syngas conditioning system 41 includes, sequentially in fluid flow communication, a Syngas Heat Recovery Steam Generator (HRSG) unit 411 for waste heat recovery, a syngas scrubber unit 421, a syngas compressor 431, a primary guard bed 436, a water gas shift reactor 441, ammonia removal unit 446, secondary guard beds 451, and a CO2/H2S removal system 461. One output of the CO2/H2S removal system 461, in the illustrated embodiment, is a syngas feed stream 470. Another output of the CO2/H2S removal system 461 is the stream 27 of recycled CO2.

As can be seen from the drawings, steam is generated from several sources inside the process. A HRSG recovers steam from the flue gas generated in the indirect fired heater unit 253 in the steam reformer unit 251. Steam is also generated in the HRSG unit 411 that recovers heat from the syngas stream 29 leaving the gasification island and steam is generated in the power boiler. The steam from all three sources are combined and superheated to provide the medium pressure steam used as the motive fluid in either syngas compressor (unit 431) steam turbine or a steam turbine power generator (FIG. 1). The combined medium pressure steam can have a biogenic content equal to the MSW feed depending on the quantity of natural gas used in firing the external heaters. In the preferred embodiment a portion of the generated syngas is fed to a gas turbine/steam turbine (combined cycle power plant) to generate a high biogenic content power that is used to supply the electrical demand of the plant. In another embodiment, all of the syngas is used to generate steam for biogenic power and to drive the syngas compressor unit 431 with a steam turbine drive.

The syngas scrubber unit 421 is a conventional gas scrubbing device that receives the syngas stream 420 and a stream 424 of caustic or other suitable alkaline solution. The liquids removed from the scrubber unit 421 comprise sour water stream 426 which can be conveyed to a wastewater treatment system. The sour water may contain undesirable contaminants such as, for example, ash particles, acids, mercury, and acidic compounds such as hydrochloric acid (HCl) and hydrogen sulfide (H2S) that are removed from the syngas. Thus, it can be appreciated that the syngas scrubber unit 421 is provided to remove contaminants that can potentially damage downstream equipment and affect the F-T synthesis catalyst performance.

Preferably, the syngas scrubber unit has three primary sections—a venturi scrubber, a packed tower section, and a direct contact cooler section. If a syngas quench cooler is utilized then approximately half of the cleaned syngas leaving the syngas scrubber unit will be circulated back to the hydrocarbon reformer quench cooler via the quench blowers while the remaining half will be compressed in the syngas compressor 431 to meet the requirements of the F-T synthesis process. If a radiant slagging cooler is employed the recycle gas blower will not be required and the flow into the scrubber will equal the flow leaving the gasification island 21. Syngas scrubbing is further described in co-pending U.S. patent application Ser. No. 14/138,635, the disclosure of which has been incorporated herein by reference. The scrubbed syngas is conveyed in stream 428.

In the illustrated embodiment, a syngas compressor stage 431 comprising one or more conventional compressor stages 433 arranged in series to raise the pressure of a compressor inlet stream comprising at least a portion of the syngas stream to a predefined level, thereby outputting a compressed syngas stream 434. In practice, the final pressure of the syngas stream 434 may range between about 400 psig to about 600 psig to meet the process requirements of the F-T synthesis process. Preferably, the heat of compression is removed with intercoolers after all but the final stage with all condensed water being collected and sent to the waste water treatment plant for recovery. The outlet of the compressor is sent hot to primary guard bed 436 where any COS and HCN is hydrolyzed to H2S and NH3 and then to the shift reactor 441.

In one embodiment, the syngas compressor drive is an extraction/condensing turbine that is driven by superheated high pressure steam with a portion of the steam extracted at low pressure for process requirements. Also, the F-T recycle compressor (unit 511 in FIG. 5) can be on the syngas compressor shaft and driven by the syngas compressor steam turbine drive. In another embodiment the syngas compressor is driven by an electric motor which is energized from the power generated in a combined cycle power plant using syngas as a fuel to produce high biogenic power.

As also shown in FIG. 3, the water gas shift reactor 441 receives a portion of the pressurized primary syngas stream 440 to shift some of the steam and CO into H2 and CO2 via the water gas shift reaction until the required H2/CO ratio in the outlet stream 450 is met. Subsequently, a side stream 442 of the pressurized primary syngas may bypass the water gas shift reactor 441 and may be recombined with an outlet stream 450 from the water gas shift reactor 441. High pressure steam is generated in the water gas shift unit to remove the shift heat of reaction. The generated steam is fed back into the syngas stream 440 feeding the reactor to provide the hydrogen source for the shift reaction. Any additional steam required can be provided by the plant steam system.

In the embodiment of FIG. 3, the outlet stream 450 of syngas from the water gas shift reactor 441 is provided to a conventional ammonia removal unit 446. In the ammonia removal unit 446, the syngas is cooled until the excess water condenses out with absorbed ammonia. Then, the syngas leaves the condenser 446 as stream 448. The sour water from the condenser 446 can be conveyed to a wastewater treatment system. The stream 448 is conveyed to the inlet of the second guard bed 451 where any volatilized Hg is removed.

As further shown in FIG. 3, the pressurized primary syngas from the second guard beds 451 is conveyed as a stream 460 to the CO2/H2S removal system 461. The CO2/H2S removal system 461 will be further described in conjunction with FIGS. 4A and 4B. One output of the CO2/H2S removal system 461 is a stream 464 of sulfur. Another output is a stream 470 of syngas from which sulfur has been removed. The third output is the CO2 recycle stream 27.

In the illustrated embodiment of FIG. 3, the syngas feed stream 470 is conveyed to H2S and final guard arsine beds 471 and, then, to an H2 recovery unit 481.

Syngas from the H2S/Arsine guard beds flows into the hydrogen recovery unit 481. The hydrogen recovery unit 481 extracts a steam 482 of high purity H2 which is required for the Hydrocracking Upgrading process, as described below. The output of the H2 recovery unit 481 is the syngas feed stream 31 to the F-T reactor 33. A third output from the hydrogen recovery unit 481 is a stream 483 of rejected syngas. The stream 483 can be recycled to join the stream 428.

In the preferred embodiment, the hydrogen recovery unit (HRU) 481 extracts H2 using a combination membrane and pressure swing adsorption ("PSA") system. The HRU membrane retentate gas is re-mixed with the bulk syngas stream and sent to the F-T Liquids Reactors. The HRU PSA purge gas is routed to the suction of the Syngas Compressor 431 and the purified H2 stream 482 is sent to upgrading.

Figure 5:
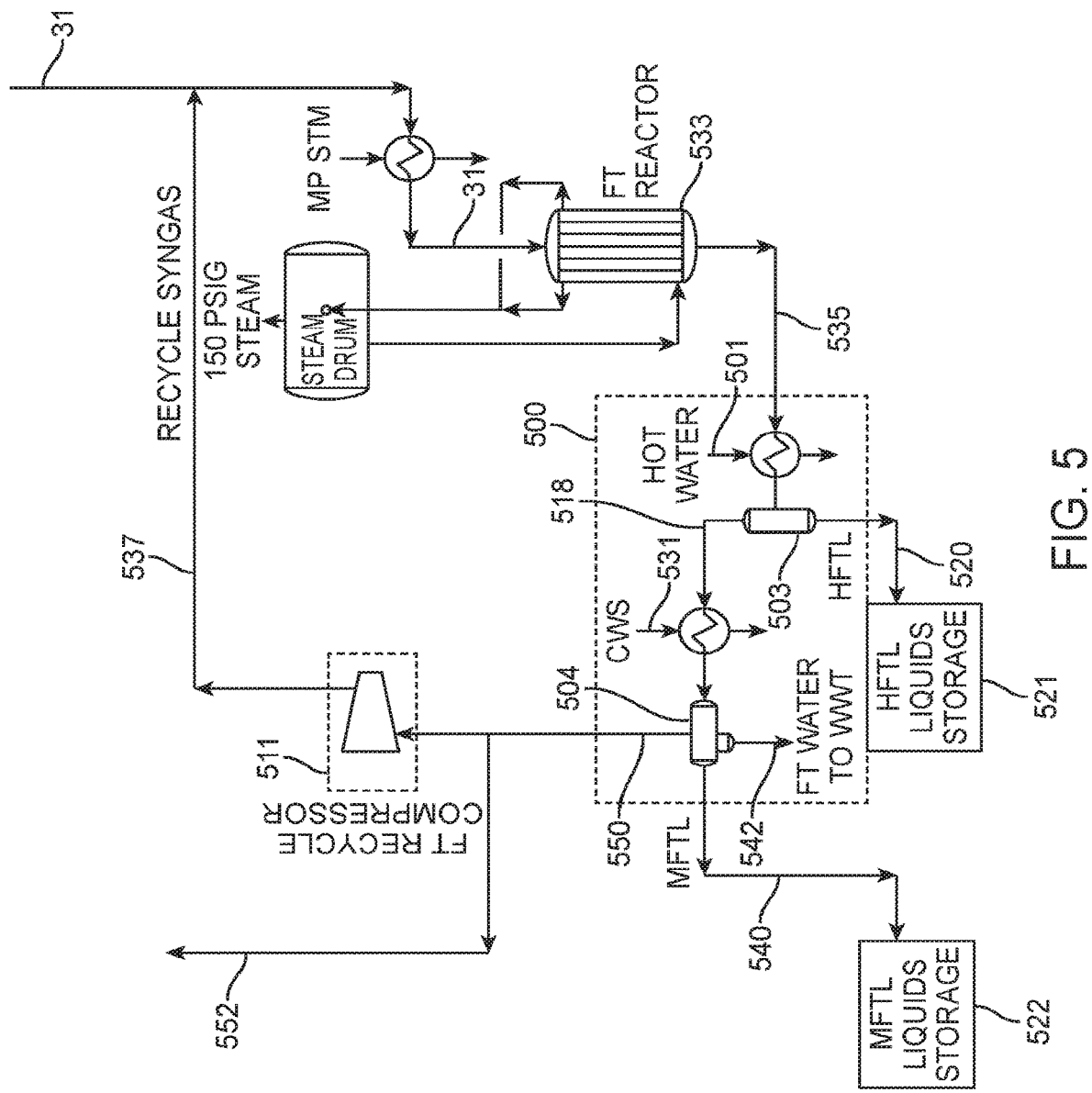

As illustrated in FIG. 5, a system 33 for generating F-T liquids receives the syngas feed stream 31. The system includes one or more F-T reactors 533 and provides, as mentioned above, the fluids output stream 535 that comprises F-T liquids and F-T tail gas. The F-T reactor output stream 535 is fed into a thermal separation system generally designated by the numeral 500 to separate the F-T liquid into its heavy F-T liquid (HFTL), medium FT liquid (MFTL), water and the F-T tail gas.

In the preferred embodiment as illustrated in FIG. 5, the thermal separation system 500 includes two condensers 501 and 531 and two separators 503 and 504. The HFTL separator 503 has outlets 518 and 520, respectively. In practice, the condenser 501 operates using a tempered hot water loop as the cooling medium to condense and separate the HFTL liquid fraction from the F-T water and MFTL liquid fraction. Both the MFTL Water and the FT Tail gas remain in a vapor phase. The HFTL stream is carried by the outlet 520 for storage in tank(s) 521 for further processing. In practice, the HFTL stream 520 is composed primarily of heavy hydrocarbon waxes which are solid at room temperature. These waxes are kept warm above 230° F. to prevent solidification.

Also as illustrated in FIG. 5, the thermal separation system 500 includes the second condenser 531 that receives, via the stream 518 from the HFTL separator 503, the F-T water and MFTL. In practice, the second condenser 531 uses cooling water to condense and separate the F-T water and MFTL from unreacted syngas and non-condensable hydrocarbons (i.e., methane, etc.). The condensed F-T water and MFTL stream phase split in the second separator 504, with the MFTL stream routed to storage unit(s) 522 via stream 540 and the F-T water routed to waste water treatment via a stream 542.

As FIG. 5 further shows, the F-T tail gas can be recycled to the F-T reactors 533 via a stream 537. In the illustrated embodiment, the F-T tail gas is separated at the MFTL separator 504 and carried by stream 550 to a compressor 511 whose output is conveyed on the syngas recycle line 537. Prior to the recycle compressor 511, a purge stream 552 branches off of stream 550. The purge stream 552 can be directed to both the hydrocarbon reformer 215 via stream 25 (FIG. 2) to control hydrocarbon content in the recycle syngas and to the power boiler to purge inerts from the recycle syngas.

Figure 6:
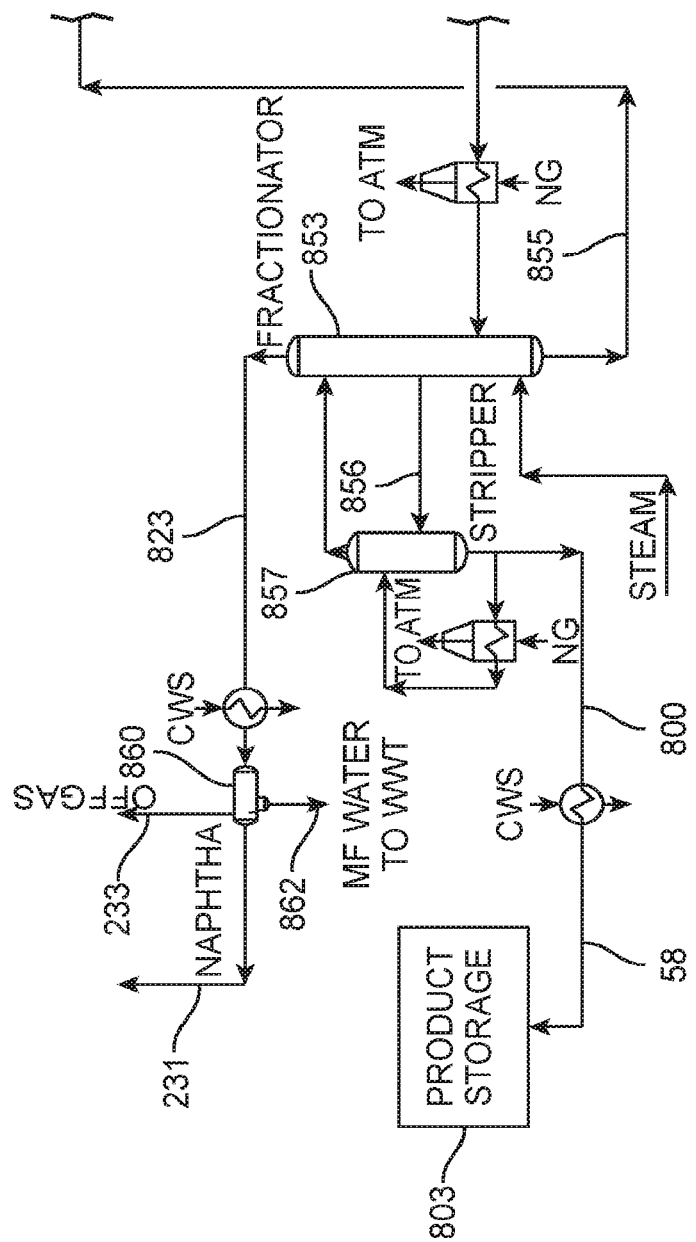
Figure 6:
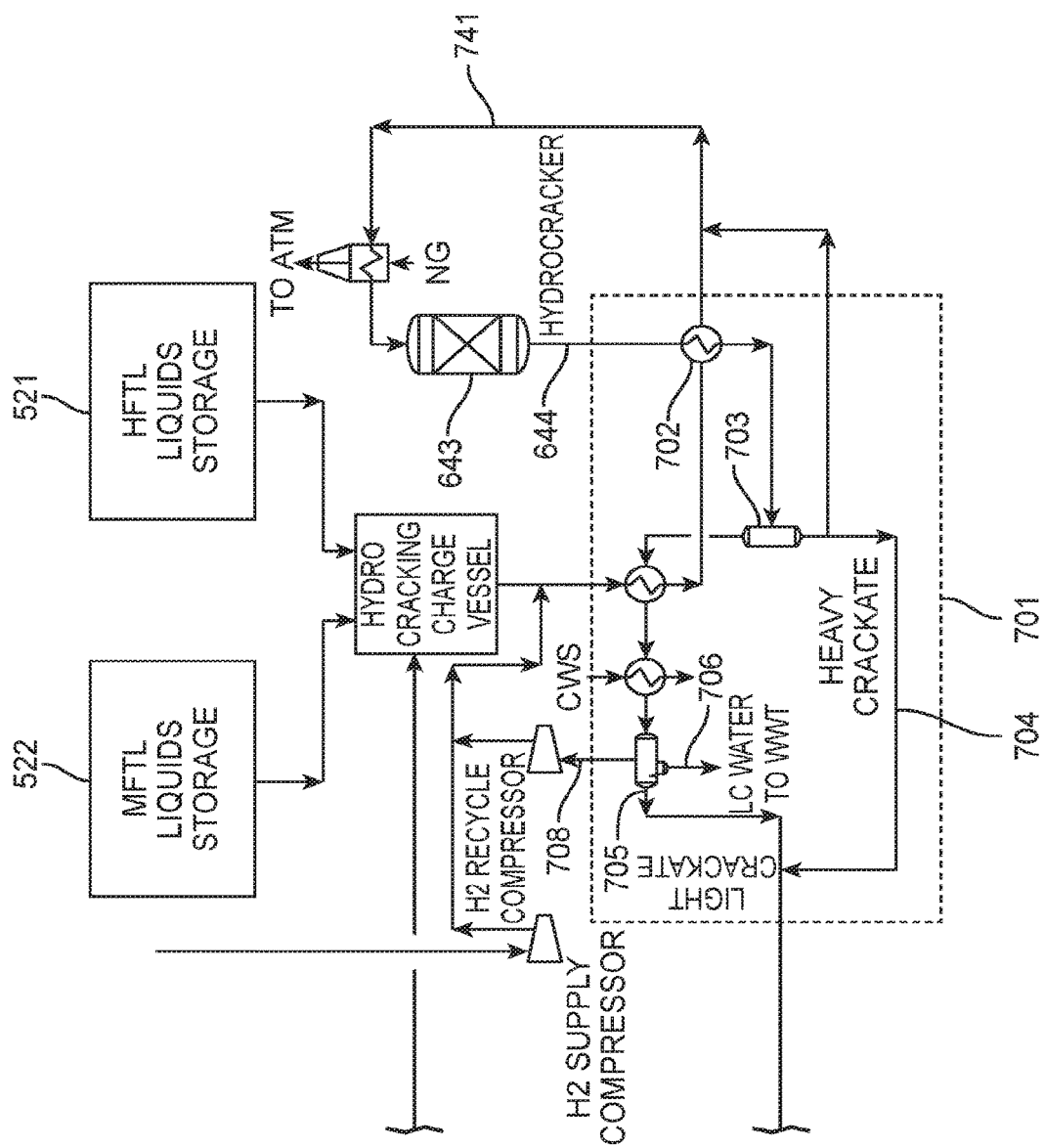

FIG. 6 shows an example of one embodiment of the upgrading system 54 of FIG. 1. More particularly, this figure illustrates a system for producing refined F-T liquids from the system of FIG. 5. The illustrated system includes a hydrocracker reactor unit 643 which receives liquids from hydrocracking charge vessel 524 fed by the aforementioned tanks 521 and 522 (FIG. 5). In the preferred embodiment, the hydrocracker reactor unit 643 employs a high temperature, high pressure catalytic process that upgrades the HFTL and MFTL hydrocarbon streams into a transportation fuel (SPK or Diesel). Due to the low severity of the upgrading, the hydro-processing and hydrocracking occur in one reactor. The olefins and alcohols are first saturated and then the alkanes are cracked into the SPK range of products. The hydrocracking mechanism, which involves a protonated cyclopropane intermediate, forms an isomer product along with a straight chained product. In the hydrocracker reactor unit 643, the feed mixture passes through a series of catalyst beds for conversion into shorter chained hydrocarbons.

In an alternative embodiment, the pre-fractionate the MFTL can be pre-fractionated and there can be removal of the light fraction overhead to the hydrocarbon reformer; then, the heavy fraction along with the HFTL would be conveyed to the hydrocracker for upgrading. This embodiment removes most of the oxygenates from the stream flowing to the hydrocracker and lessens the hydrotreating load on the hydrocracker.

As further illustrated in FIG. 6, the hydrocracker reactor unit 643 provides the output stream 644 which is fed to a hydrocarbon thermal separation system generally designated by the numeral 701 wherein the crackate is cooled, condensed, and separated into two separate heavy and light crackate streams, using a series of heat exchangers and separator vessels.

In the illustrated embodiment of the, hydrocarbon thermal separation system 701, the crackate is cooled in a feed/effluent heat exchanger 702 and the heavy crackate is separated from the light crackate in a heavy crackate separator 703. From the heavy crackate separator 703, the heavy crackate syncrude is routed to a fractionator 853, as by streams 704 and 750. In addition, some of the heavy crackate can be recycled to the hydrocracker 643 to keep material flowing into the hydrocracker during startup and when the fractionation column is malfunctioning.

In the illustrated embodiment, a light crackate separator 705 is provided for separating the light crackate from heavy crackate water and hydrogen. The separated light crackate is routed to the fractionator 853 by stream 750. The heavy crackate water is sent, as by line 706, to the bio-refinery's waste water treatment plant for treatment. The separated hydrogen gas is routed to recycle as by streams 708, 741 and 742.

The fractionation process in FIG. 6 will now be described in greater detail. As previously mentioned, the fractionator 853 receives a stream 704 of heavy crackate liquids and a stream 750 of light crackate liquids. The purpose of the fractionator 853 is to separate the SPK or Diesel cut from the heavy crackate fraction and the naphtha fraction. The side draw stream 856 is fed into a stripper column 857 to remove lights from the SPK/Diesel feed and provide final clean up and recovery of the SPK/Diesel products. In the fractionator 853, the incoming heavy and light crackate streams are combined and heated by natural gas fired heater for an initial separation in the fractionator column. Preferably, the fractionator 853 uses direct steam injection to strip the low boiling hydrocarbons from the high boiling hydrocarbons without utilizing a high temperature reboiler configuration.

The outputs from the fractionator 853 include overhead stream 23 that carries recyclable hydrocarbon products. Preferably, the overhead stream 823 which is provided into a condenser unit 860 where the stream is condensed and separated into three streams: main fractionator ("MF") water stream 862, the afore-mentioned light phase (naphtha) stream 231, and offgas stream 233. In practice, the naphtha can be refluxed back into the fractionator 53 and/or sent to a Naphtha Vaporizer for injection into the hydrocarbon reformer. The offgas stream 233 is recycled by the off gas compressor to the hydrocarbon reformer for reprocessing. The bottoms from the fractionator column 853 are pumped to the hydrocracking charge vessel 560, as by stream 855, for additional hydrocracking. MF Water is sent to the bio-refinery's wastewater treatment plant for treatment.

Naphtha from the Fractionator OH Separator is pumped into the Naphtha Vaporizer where it is vaporized using low-pressure steam. The naphtha vapor then flow into the hydrocarbon reformer 215 of FIG. 2 for recovery. The fractionation column overhead pressure floats on the offgas Compressor discharge rate. The offgas Compressor provides motive force to move the Fractionator Overhead Separator offgas into the discharge of the Naphtha Vaporizer. The combined streams then flow into the hydrocarbon reformer.

The SPK product, withdrawn by the steam 856 from the upper part of the fractionator 853, is sent to the Product Stripper column 857 for final product separation. The heat to the product Stripper column 857 is provided, for example, by a natural gas fired Product Stripper Reboiler. The Product Stripper overhead stream recycles back to the Fractionator 853. The bottoms stream 800 is cooled and sent, via the stream 58, to storage unit 803 as the SPK product.

Figure 4A:
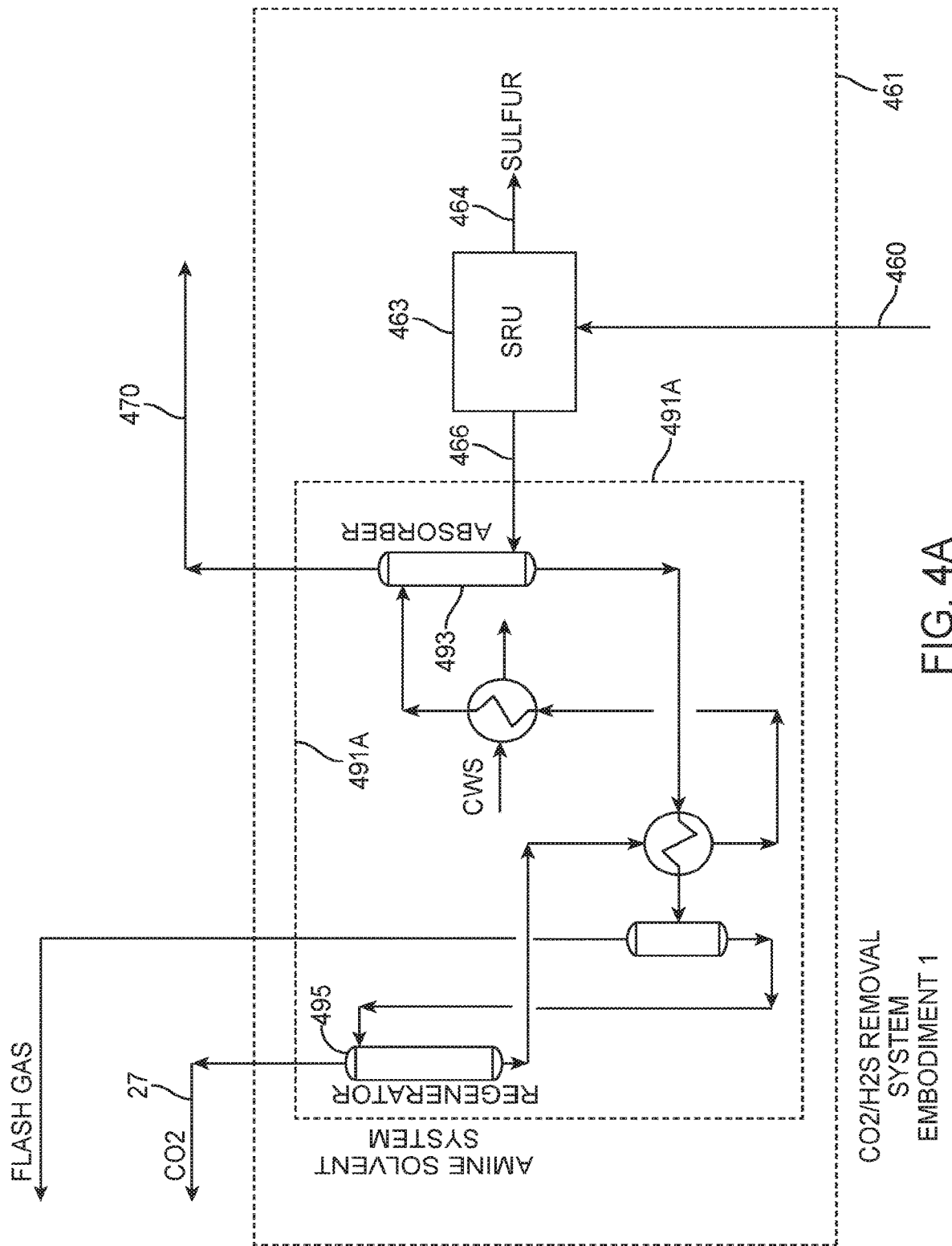

As shown in FIG. 4A, one embodiment of an exemplary CO2/H2S removal system 461 includes a sulfur removal unit 463 that receives the stream 460. One output of the sulfur removal unit 463 is a stream 464 of sulfur. Another output of the removal unit 463 is a stream 466 of syngas from which sulfurs have been removed.

The syngas stream 466 is fed to an amine solvent system, generally indicated by the numeral 491. In the illustrated embodiment, the amine solvent system 491A comprises an absorber unit 493 and a regenerator unit 495 connected in counter-current relationship. The output of the regenerator unit 493 is the aforementioned syngas feed stream 470. The output of the absorber unit 495 is the aforementioned stream 27 of recycled CO2.

In the preferred embodiment of FIG. 4A, the absorber unit 493 is a column where CO2 is removed by contact with a circulating amine/water solution. In this embodiment the amine absorber can remove H2S from stream 466 in the event the sulfur removal unit under performs. The treated syngas is water washed to remove any entrained amine solution. In the preferred embodiment, the cleaned syngas leaving the solvent absorber 493 is heated using Medium Pressure (MP) saturated steam and routed, as stream 470, to the guard bed to removal trace H2S and arsenic catalyst poisons prior to introduction into the F-T synthesis process.

Figure 4B:
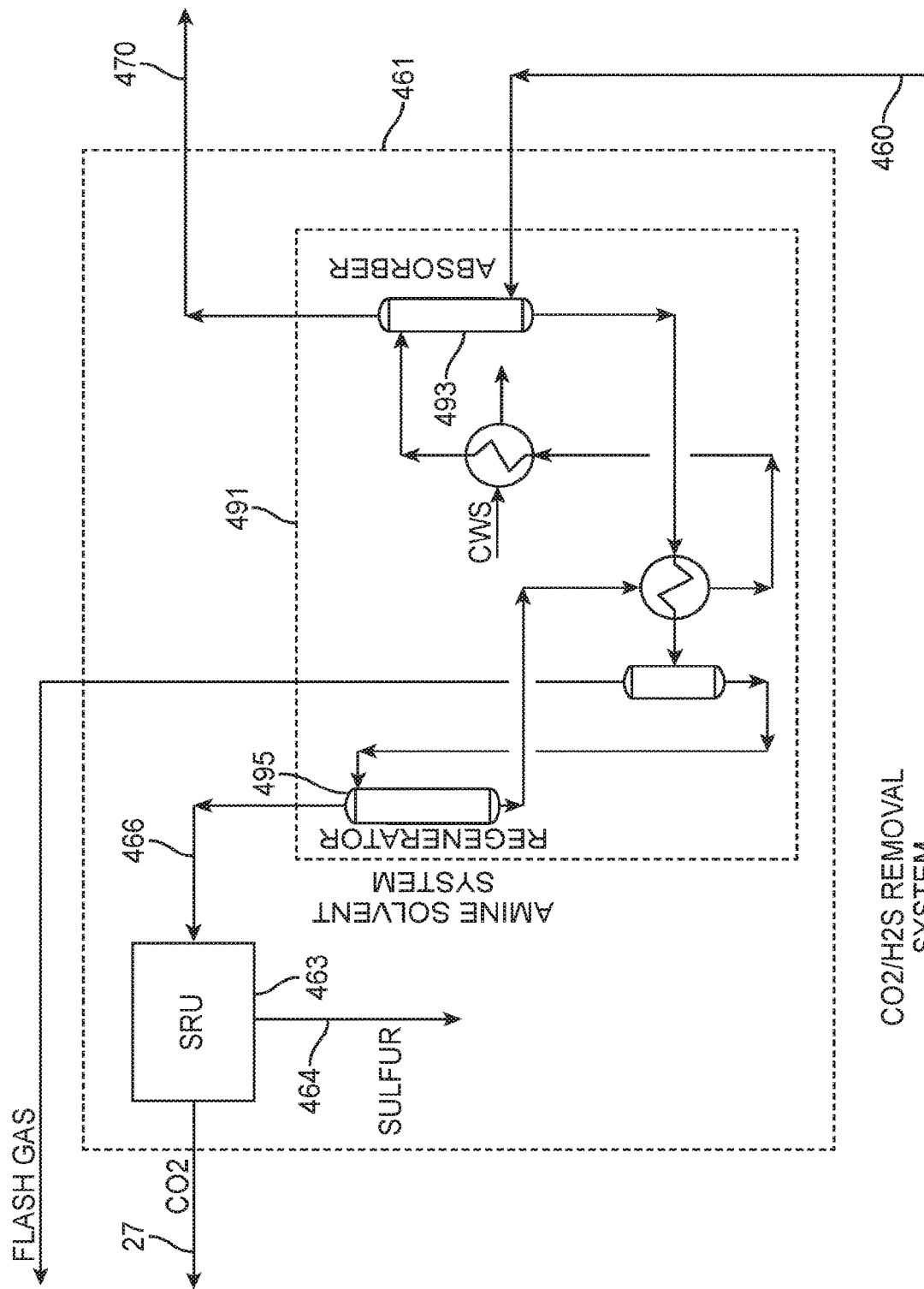

As shown in FIG. 4B, another exemplary CO2/H2S removal system 461 includes an amine unit where syngas stream 460 is fed to an amine solvent system, generally indicated by the numeral 491B. In the illustrated embodiment, the amine solvent system 491B comprises an absorber unit 493 and a regenerator unit 495 connected in counter-current relationship. The output of the regenerator unit 495 is fed to the sulfur removal unit 463. The output of the absorber unit 493 is the aforementioned syngas feed stream 470. In this embodiment, the absorber unit 493 is a column where CO2 and H2S is removed by contact with a circulating amine/water solution. The treated syngas is then water washed to remove any entrained amine solution and sent, as stream 470, to the final guard beds 471.

In embodiment of FIG. 4B, the regenerator overhead output stream 466 is fed to the sulfur removal unit 463 where the H2S is removed from the reject CO2 stream. One output of the sulfur removal unit 463 is the aforementioned stream 27 of recycled CO2 and a stream 464 of sulfur. A portion of the overhead CO2 reject stream from the Sulfur Removal unit is compressed and recycled back the gasification island and the excess is vented to the atmosphere.

In operation of CO2/H2S removal system in FIGS. 4A and 4B, "rich" amine (i.e., amine after absorption of CO2) from the absorber column passes through a lean/rich exchanger and then flashes into the Rich Solvent Flash Drum. The flashed gas, rich in CO and H2, flows to the suction of the syngas compressor for reuse in the process. The flashed rich liquid stream flows to the Solvent Regenerator column. In the Solvent Regenerator, the rich solvent is heated in a steam reboiler, driving off the absorbed CO2/H2S. The "leaned" solvent flowing out the bottom of the Solvent Regenerator is recirculated back via the lean/rich exchanger and the solvent cooler to the Absorber for reuse. A portion of the overhead CO2 reject stream from the Solvent Regenerator is compressed and recycled back the gasification island and the excess is vented to the atmosphere. Preferably, the system is designed to reduce the CO2 content in the syngas stream to <1 mol % and the H2S content to <5 ppmv, while minimizing the loss of CO and H2.

In the overall operation of the above-described system, multiple reactions take place as MSW is gasified. The major reaction occurs at elevated temperatures when char (carbon) reacts with steam to produce syngas primarily made up of hydrogen (H2), carbon monoxide (CO), carbon dioxide (CO2), and some hydrocarbons:

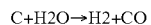
$$C+H2O \rightarrow H2+CO$$

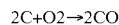
$$2C+O2 \rightarrow 2CO$$

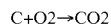
$$C+O2 \rightarrow CO2$$

Simultaneously, the reversible "water gas shift" reaction

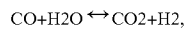
$$CO+H2O \leftrightarrow CO2+H2,$$

approaches equilibrium conditions with the CO/H2O and the CO2/H2 ratios based on the equilibrium constant at the gasifier operating temperature. The gasification system may be configured, and conditions provided, so that at least the following gasification reaction occurs:

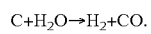
$$C+H_2O \rightarrow H_2+CO.$$

Simultaneously, conditions may preferably be provided so that the following reversible "water shift" reaction reaches an equilibrium state determined mainly by the temperature of the gasifier, the pressure preferably being near atmospheric:

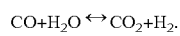
$$CO+H_2O \leftrightarrow CO_2+H_2.$$

The primary FT reaction converts syngas to higher molecular weight hydrocarbons and water in the presence of a catalyst:

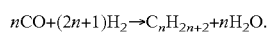
$$nCO+(2n+1)H_2 \rightarrow C_nH_{2n+2}+nH_2O.$$

Further as to the overall operation of system, it should be noted that the syngas produced in the gasification island 21 has an insufficient quantity of hydrogen for the effective production and upgrading of F-T liquids. The Sour shift reactor 441 generates additional hydrogen to increase the $H_2$:CO ratio in the syngas from about 0.8 to approximately 2.0. The water gas shift reaction converts a portion of the CO and $H_2O$ in the syngas to $H_2$ and $CO_2$. The reaction is exothermic and occurs over a sour shift catalyst. The reaction is a "sour shift" as $H_2S$ is still present in the syngas stream. Utility steam and steam generated by the Shift Reactor 441 are mixed with the syngas to provide the water for the water-gas shift reaction and to moderate the temperature rise in the reactor. Hydrogen production and the syngas $H_2$:CO ratio are controlled by bypassing a portion of the syngas stream around the Shift Reactor. The Shift Reactor effluent heat is recovered by interchanging with the reactor influent syngas, generating shift reactor steam, and pre-heating boiler feed water.

The creation of fuel from MSW by the above-described system has significant advantages. It provides an energy efficient system with a very low emissions profile, reduces MSW entering landfills (thus dramatically reducing harmful methane gas emissions from landfills and mitigating the need for new or expanded landfills), reduces by displacement greenhouse gases associated with the use of petroleum and coal derived fuel products. The system increase the biogenic content of cellulosic-based fuels and, therefore, substantially increases the value of such fuels.

Exemplary embodiments have been described with reference to specific configurations. The foregoing description of specific embodiments and examples has been presented for the purpose of illustration and description only, and although the invention has been illustrated by certain of the preceding examples, it is not to be construed as being limited thereby.

What is claimed is:

1. A process for producing a transportation fuel or fuel additive derived from municipal solid wastes (MSW) that contain materials that are produced from biogenic derived carbon materials and non-biogenic derived carbon materials and where the MSW is processed to produce a processed MSW feedstock that contains a higher concentration of biogenic carbon materials than non-biogenic carbon materials, the process comprising the steps of:
- a) converting the processed MSW feedstock into Fischer-Tropsch liquids in a bio-refinery while maintaining a greater concentration of biogenic carbon than non-biogenic carbon; and
- b) upgrading the Fischer-Tropsch liquids into a transportation fuel or fuel additive while maintaining a greater concentration of biogenic carbon than non-biogenic carbon.

2. The process according to claim 1 wherein the step of converting the processed MSW feedstock into Fischer-Tropsch liquids in the bio-refinery, further comprises:
converting the processed MSW feedstock in a gasification island.

3. The process according to claim 1, further comprising the step of:
in a power generation process, converting at least a portion of the biogenic carbon material into biogenic carbon derived power.

4. The process according to claim 1, wherein the converting step is comprised of: three stages carried out in a gasification island:
1) steam reforming the processed feedstock in a steam reformer configured to dry, volatilize and gasify the processed MSW feedstock to produce syngas containing CO, $H_2$, $H_2O$ and $CO_2$, unreacted char, inert solids and unreacted hydrocarbons;
2) further gasifying in a sub-stoichiometric carbon oxidation unit configured to gasify the unreacted char from the steam reformer; and
3) hydrocarbon reforming in a hydrocarbon reforming unit configured to convert remaining char, hydrocarbons and tars into syngas.

5. The process according to claim 4, further comprising:
conditioning the syngas in a syngas conditioning unit configured to receive the syngas from the gasification island and remove contaminants, remove/recover $CO_2$ and provide a biogenic $CO_2$ recycle stream for recycling biogenic $CO_2$ to the gasification island for biogenic carbon conservation and to adjust the $H_2:CO_2$ ratio in the syngas to a predetermined value; and
converting the syngas into Fischer-Tropsch liquids in one or more F-T reactors;
separating the F-T liquids in a separation system into heavy F-T liquids (HFTL) and medium F-T liquids (MFTL); and
upgrading the separated F-T liquids in an upgrading system comprising a hydrotreating/hydrocracking reactor and fractionation system configured to upgrade the HFTL and MFTL into a transportation fuel.

6. A process for producing Fischer-Tropsch (F-T) liquids derived from municipal solid wastes (MSW) that contain materials that are produced from biogenic derived carbon materials and non-biogenic derived carbon materials and where the MSW is processed to produce a processed MSW feedstock that contains a higher concentration of biogenic carbon materials than non-biogenic carbon materials, the process comprising
converting the processed MSW feedstock into Fischer-Tropsch liquids in a bio-refinery while maintaining a greater concentration of biogenic carbon than non-biogenic carbon.

7. The process according to claim 6, wherein the converting step is comprised of three stages carried out in a gasification island:
1) steam reforming the processed feedstock in a steam reformer configured to dry, volatilize and gasify the processed feedstock to produce syngas containing CO, $H_2$, $H_2O$ and $CO_2$, unreacted char, inert solids and unreacted hydrocarbons;
2) further gasifying in a sub-stoichiometric carbon oxidation unit configured to gasify the unreacted char from the steam reformer; and
3) hydrocarbon reforming in a hydrocarbon reforming unit configured to convert remaining char, hydrocarbons and tars into syngas.

8. The process according to claim 7, further comprising:
conditioning the syngas in a syngas conditioning unit configured to receive the syngas from the gasification island and remove contaminants, remove/recover $CO_2$ and provide a biogenic $CO_2$ recycle stream for recycling biogenic $CO_2$ to the gasification island for biogenic carbon conservation and to adjust the $H_2:CO_2$ ratio in the syngas to a predetermined value; and
converting the syngas into Fischer-Tropsch liquids in one or more F-T reactors.

9. The process according to claim 6, further comprising the step of:
in a power generation process, converting at least a portion of the biogenic carbon material into biogenic carbon derived power.

* * * * *